US010385325B2

(12) United States Patent
Fukui et al.

(10) Patent No.: US 10,385,325 B2
(45) Date of Patent: Aug. 20, 2019

(54) METHOD FOR PRODUCTION OF RECOMBINANT HUMAN ALPHA-GALACTOSIDASE A FROM MATERIAL CONTAINING CONTAMINANT HOST CELL PROTEINS BY CHROMATOGRAPHY

(71) Applicant: JCR Pharmaceuticals Co., Ltd., Ashiya-shi, Hyogo (JP)

(72) Inventors: Tsuyoshi Fukui, Kobe (JP); Atsuko Kawasaki, Kobe (JP); Yukichi Hatano, Kobe (JP); Yae Ito, Kobe (JP); Kazutoshi Mihara, Kobe (JP); Atsushi Sugimura, Kobe (JP)

(73) Assignee: JCR PHARMACEUTICALS CO., LTD., Hyogo (JP)

( * ) Notice: Subject to any disclaimer, the term of this patent is extended or adjusted under 35 U.S.C. 154(b) by 0 days.

(21) Appl. No.: 15/545,194

(22) PCT Filed: Jan. 21, 2016

(86) PCT No.: PCT/JP2016/000296
§ 371 (c)(1),
(2) Date: Jul. 20, 2017

(87) PCT Pub. No.: WO2016/117341
PCT Pub. Date: Jul. 28, 2016

(65) Prior Publication Data
US 2018/0016564 A1 Jan. 18, 2018

(30) Foreign Application Priority Data
Jan. 22, 2015 (WO) .................. PCT/JP2015/000290

(51) Int. Cl.
C12N 9/40 (2006.01)
A61K 38/00 (2006.01)

(52) U.S. Cl.
CPC .... *C12N 9/2465* (2013.01); *C12Y 302/01022* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,356,804 A * | 10/1994 | Desnick | A61K 35/18 435/208 |
| 9,617,529 B2 * | 4/2017 | Asano | C12N 9/2465 |
| 2002/0146771 A1 | 10/2002 | Burg et al. | |

FOREIGN PATENT DOCUMENTS

| WO | 9011353 A1 | 10/1990 |
|---|---|---|
| WO | 9412628 A1 | 6/1994 |
| WO | 9811206 A2 | 3/1998 |
| WO | 0053730 A2 | 9/2000 |
| WO | 2006051070 A1 | 5/2006 |
| WO | 2011108451 A1 | 9/2011 |
| WO | 2014016873 A1 | 1/2014 |
| WO | 2014017088 A1 | 1/2014 |

OTHER PUBLICATIONS

Deer et al. Biotechnol Prog. May-Jun. 2004;20(3):880-9. (Year: 2004).*
Corchero et al., "Integrated approach to produce a recombinant, his-tagged human α-galactosidase a in mammalian cells", Biotec. Prog., 27 (5), p. 1206-1217 (2011), 12 pages.
Ioannou et al., "Overexpression of human alpha-galactosidase A results in its intracellular aggregation, crystallization in lysosomes, and selective secretion", J. Cell Biol., 119(5), p. 1137-1150 (1992), 14 pages.
Lee et al,; "A biochemical and pharmacological comparison of enzyme replacement therapies for the glycolipid storage disorder Fabry disease", Glycobiology, 13(4), 305-313 (2003), 9 pages.
Mapes et al., Science, vol. 169, Sep. 4, 1970, pp. 987-989, 3 pages.
Brady et al., "Replacement Therapy for Inherited Enzyme Deficiency", The New England Journal of Medicine; vol. 289 No. 1, Jul. 5, 1973, pp. 9-14, 6 pages.
Desnick et al., "Enzyme therapy in Fabry disease: differential in vivo plasma clearance and metabolic effectiveness of plasma and splenic a-galactosidase A isozymes", Proc Natl Acad Sci USA, Medical Sciences, vol. 76, No. 10, pp. 5326-5330, Oct. 1979, 5 pages.
Bishop et al., "Human alpha-galactosidase A: nucleotide sequence of a cDNA clone encoding the mature enzyme", Proc. Natl. Acad. Sci. USA, vol. 83, pp. 4859-4863, Jul. 1986, Genetics, 5 pages.
Bishop et al.,"Human α-Galactosidase: Characterization and Eukaryotic Expression of the Full-Length cDNA and Structural Organization of the Gene", Lipid Storage Disorders Biological and Medical Aspects, Series A: Life Sciences vol. 150, pp. 809-823 1988 15 pages.
International Search Report (English) and Written Opinion of International Application No. PCT/JP2016/00296, dated Apr. 19, 2016, 9 pages provided.
International Search Report (English) and Written Opinion of International Application No. PCT/JP2015/00290, dated Apr. 21, 2015, 8 pages provided.

* cited by examiner

*Primary Examiner* — Christian L Fronda
(74) *Attorney, Agent, or Firm* — Hamre, Schumann, Mueller & Larson, P.C.

(57) ABSTRACT

Disclosed is a method for production of recombinant human alpha-galactosidase A (rh alpha-Gal A) in a large scale, with a high purity. The method comprises the steps of (a) culturing rh alpha-Gal A-producing mammalian cells in a serum-free medium, (b) collecting culture supernatant, (c) subjecting the culture supernatant to anion-exchange column chromatography, (d) to hydrophobic column chromatography, (e) to a column chromatography employing as solid phase a material having affinity for phosphate group, (f) to cation-exchange column chromatography, (g) to dye-affinity column chromatography, and (h) to gel filtration column chromatography, in the order.

8 Claims, 5 Drawing Sheets

Specification includes a Sequence Listing.

[Fig. 1]
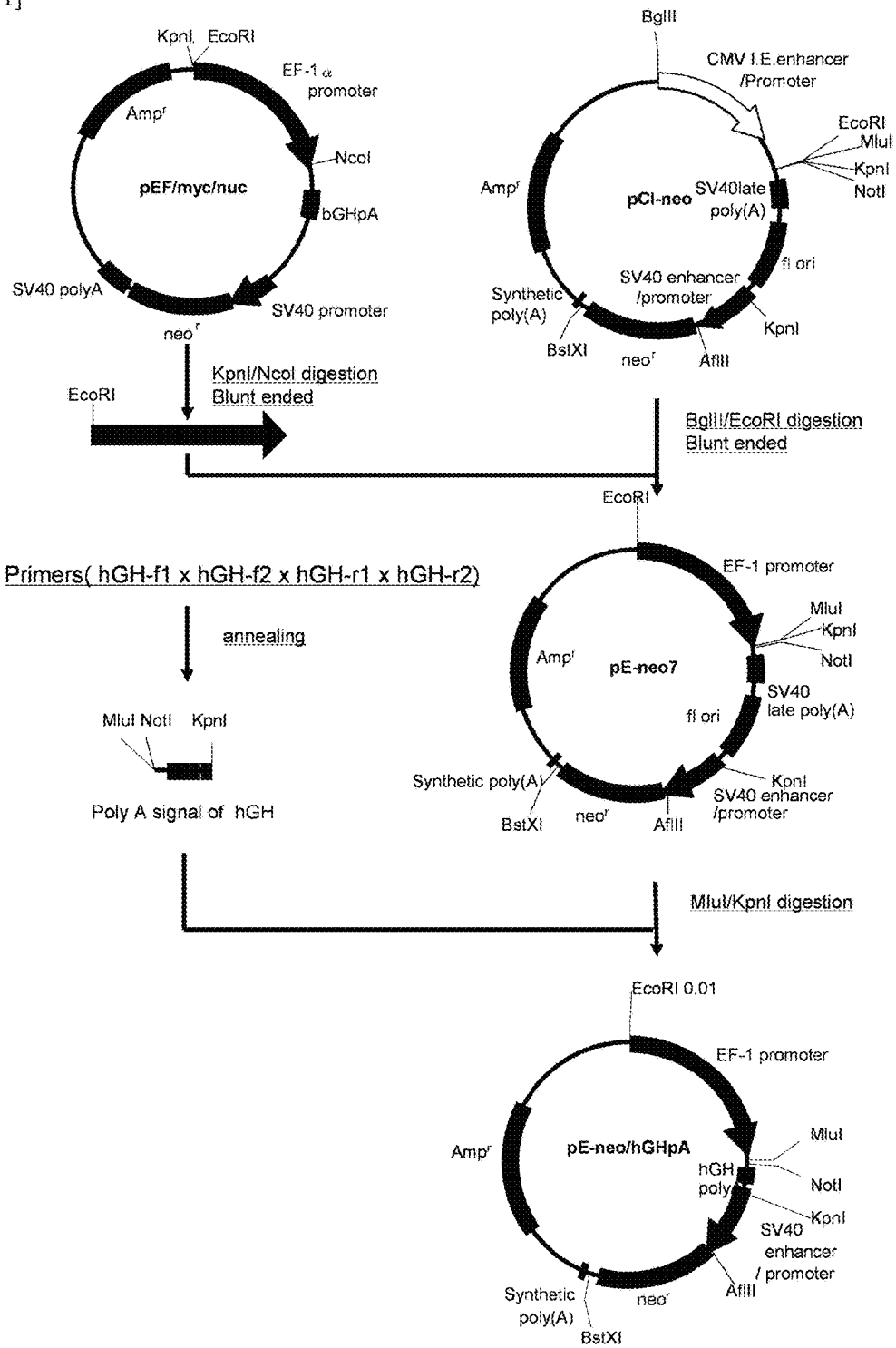

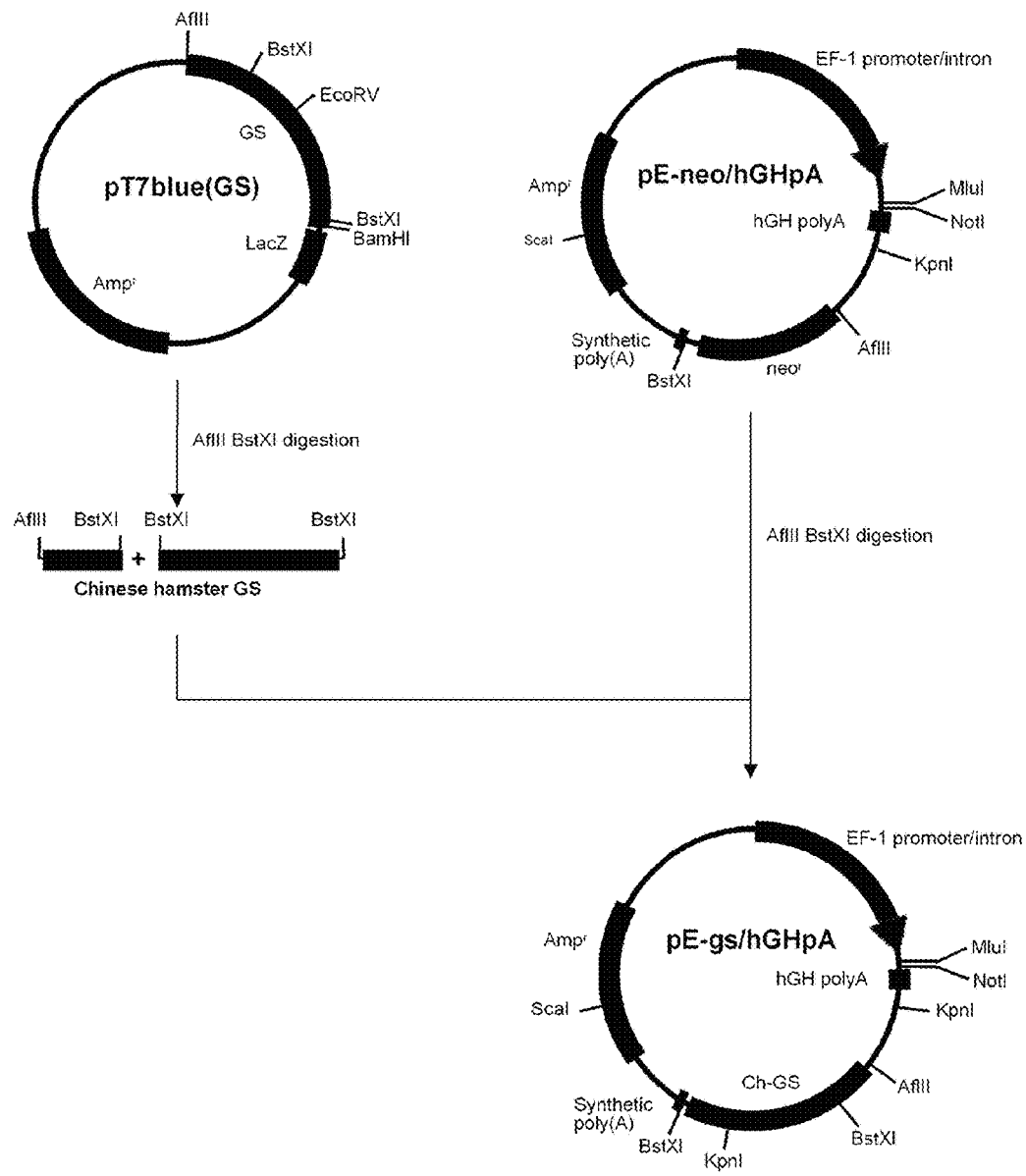

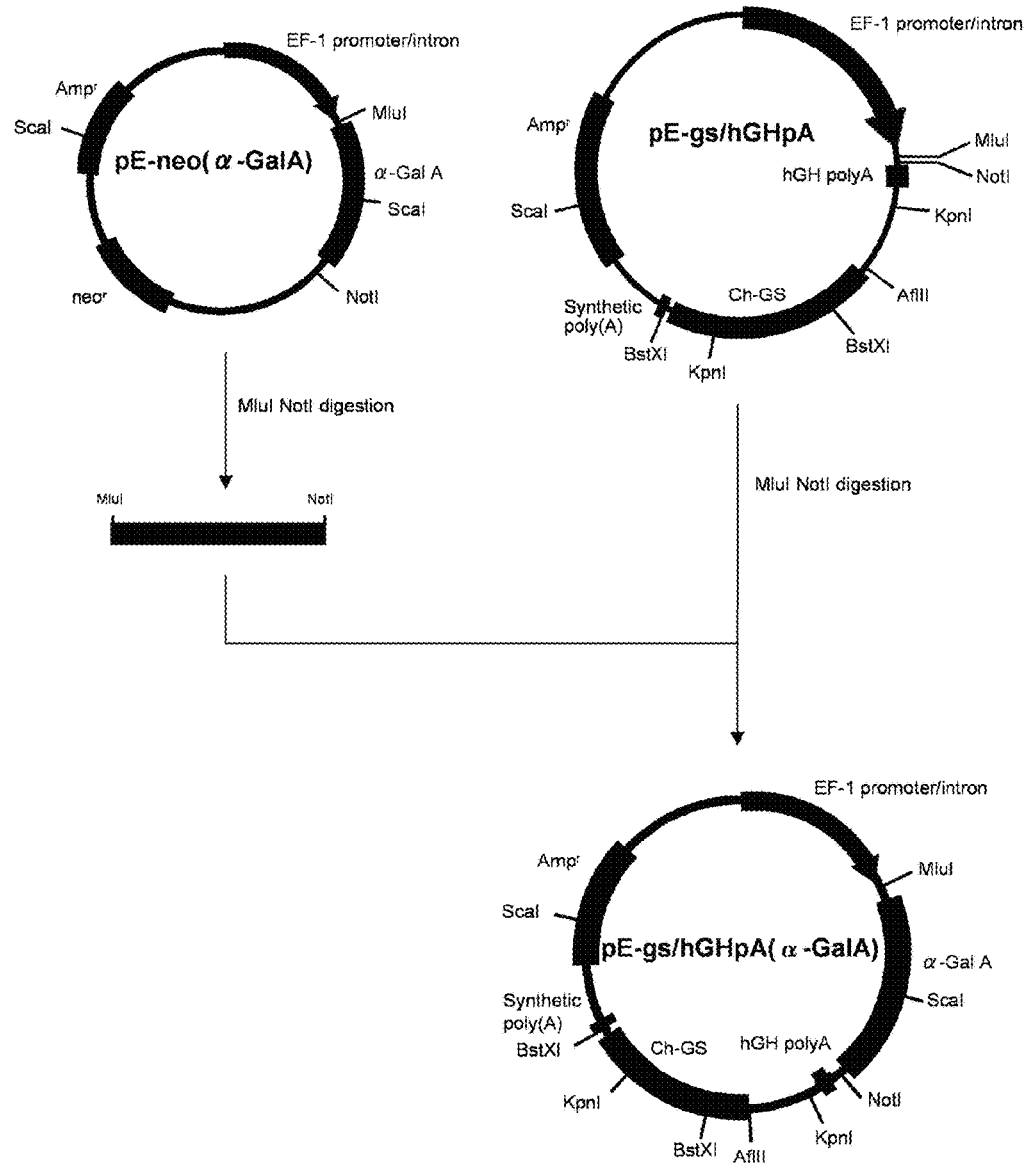
[Fig. 2-2]

[Fig. 3]
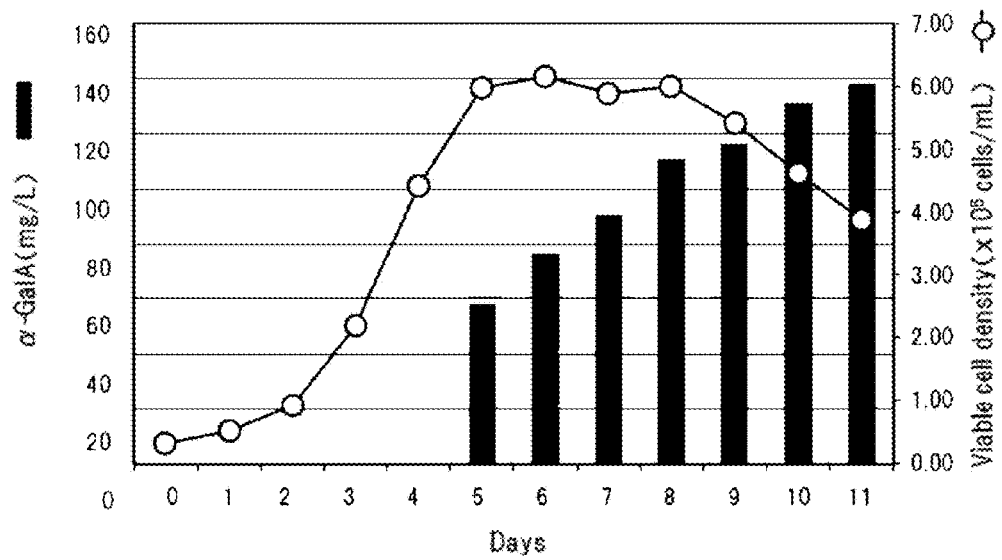
[Fig. 4]
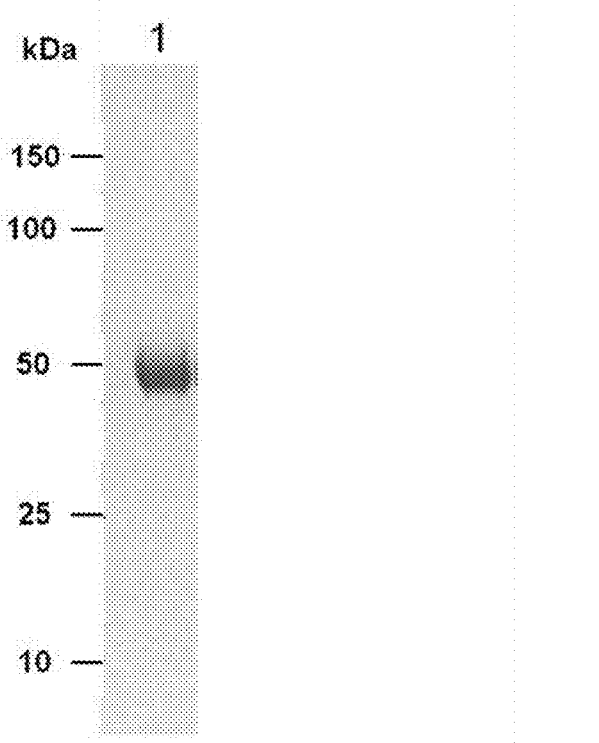

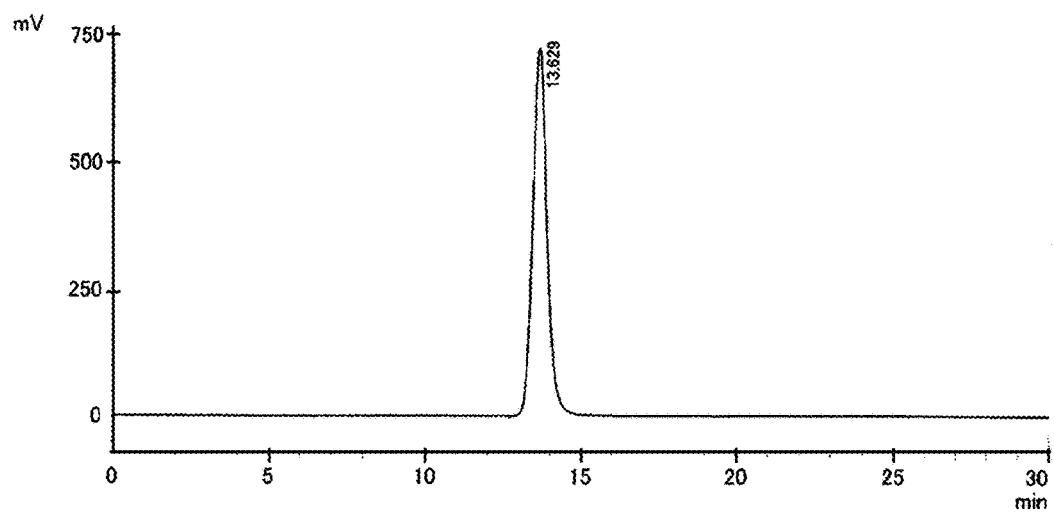
[Fig. 5]

SEQUENCE LISTING

<160> NUMBER OF SEQ ID NOS: 14

<210> SEQ ID NO 1
<211> LENGTH: 114
<212> TYPE: DNA
<213> ORGANISM: Artificial Sequence
<220> FEATURE:
<223> OTHER INFORMATION: hGH-f1, synthetic sequence

<400> SEQUENCE: 1
cgcgtgaatt cgcggccgct ctagacccgg gtggcatccc tgtgaccct ccccagtgcc      60 tctcctggcc ctggaagttg ccactccagt gcccaccagc cttgtcctaa taaa          114

<210> SEQ ID NO 2
<211> LENGTH: 124
<212> TYPE: DNA
<213> ORGANISM: Artificial Sequence
<220> FEATURE:
<223> OTHER INFORMATION: hGH-r1, synthetic sequence

<400> SEQUENCE: 2
tgatgcaact taattttatt aggacaaggc tggtgggcac tggagtggca acttccaggg     60
ccaggagagg cactggggag gggtcacagg gatgccaccc gggtctagag cggccgcgaa    120
ttca                                                                 124

<210> SEQ ID NO 3
<211> LENGTH: 96
<212> TYPE: DNA
<213> ORGANISM: Artificial Sequence
<220> FEATURE:
<223> OTHER INFORMATION: hGH-f2, synthetic sequence

<400> SEQUENCE: 3
attaagttgc atcattttgt ctgactaggt gtccttctat aatagcgcag caccatggcc    60
tgaaataacc tctgaaagag gaacttggtt aggtac                              96

<210> SEQ ID NO 4
<211> LENGTH: 78
<212> TYPE: DNA
<213> ORGANISM: Artificial Sequence
<220> FEATURE:
<223> OTHER INFORMATION: hGH-r2, synthetic sequence

<400> SEQUENCE: 4
ctaaccaagt tcctctttca gaggttattt caggccatgg tgctgcgcta ttatagaagg    60
acacctagtc agacaaaa                                                  78

<210> SEQ ID NO 5
<211> LENGTH: 25
<212> TYPE: DNA
<213> ORGANISM: Artificial Sequence
<220> FEATURE:
<223> OTHER INFORMATION: Primer GS-1, synthetic sequence

<400> SEQUENCE: 5
cttaagatgg ccacctcagc aagtt                                          25

<210> SEQ ID NO 6
<211> LENGTH: 27
<212> TYPE: DNA
<213> ORGANISM: Artificial Sequence
<220> FEATURE:
<223> OTHER INFORMATION: Primer GS-3, synthetic sequence

<400> SEQUENCE: 6
acgatatccc tgccataggc tttgtct                                        27

<210> SEQ ID NO 7
<211> LENGTH: 27
<212> TYPE: DNA
<213> ORGANISM: Artificial Sequence
<220> FEATURE:
<223> OTHER INFORMATION: Primer GS-2, synthetic sequence

<400> SEQUENCE: 7
agacaaagcc tatggcaggg atatcgt                                        27

<210> SEQ ID NO 8
<211> LENGTH: 30
<212> TYPE: DNA
<213> ORGANISM: Artificial Sequence
<220> FEATURE:
<223> OTHER INFORMATION: Primer GS-4, synthetic sequence

<400> SEQUENCE: 8
ccatcgtgat ggttagtttt tgtattggaa                                     30

<210> SEQ ID NO 9
<211> LENGTH: 26
<212> TYPE: DNA
<213> ORGANISM: Artificial Sequence
<220> FEATURE:
<223> OTHER INFORMATION: Primer GAL-Mlu, synthetic sequence

<400> SEQUENCE: 9
ggtacgcgtg acaatgcagc tgagga                                         26

<210> SEQ ID NO 10
<211> LENGTH: 21
<212> TYPE: DNA
<213> ORGANISM: Artificial Sequence
<220> FEATURE:
<223> OTHER INFORMATION: Primer GAL-Sca2, synthetic sequence

<400> SEQUENCE: 10
gtgattgcag tactgtcgga t                                              21

<210> SEQ ID NO 11
<211> LENGTH: 21
<212> TYPE: DNA
<213> ORGANISM: Artificial Sequence
<220> FEATURE:
<223> OTHER INFORMATION: Primer GAL-Sca1, synthetic sequence

<400> SEQUENCE: 11
atccgacagt actgcaatca c                                              21

<210> SEQ ID NO 12
<211> LENGTH: 35
<212> TYPE: DNA
<213> ORGANISM: Artificial Sequence
<220> FEATURE:
<223> OTHER INFORMATION: Primer GAL-Xba, synthetic sequence

<400> SEQUENCE: 12
gagtctagat tttaaagtaa gtcttttaat gacat                               35

<210> SEQ ID NO 13
<211> LENGTH: 1290
<212> TYPE: DNA
<213> ORGANISM: Homo sapiens
<220> FEATURE:
<221> NAME/KEY: CDS
<222> LOCATION: (1)..(1290)

<400> SEQUENCE: 13

```
atg cag ctg agg aac cca gaa cta cat ctg ggc tgc gcg ctt gcg ctt     48
Met Gln Leu Arg Asn Pro Glu Leu His Leu Gly Cys Ala Leu Ala Leu
1               5                   10                  15 cgc ttc ctg gcc ctc gtt tcc tgg gac atc cct ggg gct aga gca ctg     96
Arg Phe Leu Ala Leu Val Ser Trp Asp Ile Pro Gly Ala Arg Ala Leu
            20                  25                  30 gac aat gga ttg gca agg acg cct acc atg ggc tgg ctg cac tgg gag    144
Asp Asn Gly Leu Ala Arg Thr Pro Thr Met Gly Trp Leu His Trp Glu
        35                  40                  45 cgc ttc atg tgc aac ctt gac tgc cag gaa gag cca gat tcc tgc atc    192
Arg Phe Met Cys Asn Leu Asp Cys Gln Glu Glu Pro Asp Ser Cys Ile
    50                  55                  60 agt gag aag ctc ttc atg gag atg gca gag ctc atg gtc tca gaa ggc    240
Ser Glu Lys Leu Phe Met Glu Met Ala Glu Leu Met Val Ser Glu Gly
65                  70                  75                  80 tgg aag gat gca ggt tat gag tac ctc tgc att gat gac tgt tgg atg    288
Trp Lys Asp Ala Gly Tyr Glu Tyr Leu Cys Ile Asp Asp Cys Trp Met
                85                  90                  95 gct ccc caa aga gat tca gaa ggc aga ctt cag gca gac cct cag cgc    336
Ala Pro Gln Arg Asp Ser Glu Gly Arg Leu Gln Ala Asp Pro Gln Arg
            100                 105                 110 ttt cct cat ggg att cgc cag cta gct aat tat gtt cac agc aaa gga    384
Phe Pro His Gly Ile Arg Gln Leu Ala Asn Tyr Val His Ser Lys Gly
```

|   |   |   |   |   |   |   |   |   |   |   |   |   |   |   |   |   |
|---|---|---|---|---|---|---|---|---|---|---|---|---|---|---|---|---|
| | | 115 | | | | | 120 | | | | | 125 | | | | |
| ctg | aag | cta | ggg | att | tat | gca | gat | gtt | gga | aat | aaa | acc | tgc | gca | ggc | 432 |
| Leu | Lys | Leu | Gly | Ile | Tyr | Ala | Asp | Val | Gly | Asn | Lys | Thr | Cys | Ala | Gly | |
| | 130 | | | | | 135 | | | | | 140 | | | | | |
| ttc | cct | ggg | agt | ttt | gga | tac | tac | gac | att | gat | gcc | cag | acc | ttt | gct | 480 |
| Phe | Pro | Gly | Ser | Phe | Gly | Tyr | Tyr | Asp | Ile | Asp | Ala | Gln | Thr | Phe | Ala | |
| 145 | | | | | 150 | | | | | 155 | | | | | 160 | |
| gac | tgg | gga | gta | gat | ctg | cta | aaa | ttt | gat | ggt | tgt | tac | tgt | gac | agt | 528 |
| Asp | Trp | Gly | Val | Asp | Leu | Leu | Lys | Phe | Asp | Gly | Cys | Tyr | Cys | Asp | Ser | |
| | | | 165 | | | | | 170 | | | | | 175 | | | |
| ttg | gaa | aat | ttg | gca | gat | ggt | tat | aag | cac | atg | tcc | ttg | gcc | ctg | aat | 576 |
| Leu | Glu | Asn | Leu | Ala | Asp | Gly | Tyr | Lys | His | Met | Ser | Leu | Ala | Leu | Asn | |
| | | 180 | | | | | 185 | | | | | 190 | | | | |
| agg | act | ggc | aga | agc | att | gtg | tac | tcc | tgt | gag | tgg | cct | ctt | tat | atg | 624 |
| Arg | Thr | Gly | Arg | Ser | Ile | Val | Tyr | Ser | Cys | Glu | Trp | Pro | Leu | Tyr | Met | |
| | | | 195 | | | | | 200 | | | | | 205 | | | |
| tgg | ccc | ttt | caa | aag | ccc | aat | tat | aca | gaa | atc | cga | cag | tac | tgc | aat | 672 |
| Trp | Pro | Phe | Gln | Lys | Pro | Asn | Tyr | Thr | Glu | Ile | Arg | Gln | Tyr | Cys | Asn | |
| | 210 | | | | | 215 | | | | | 220 | | | | | |
| cac | tgg | cga | aat | ttt | gct | gac | att | gat | gat | tcc | tgg | aaa | agt | ata | aag | 720 |
| His | Trp | Arg | Asn | Phe | Ala | Asp | Ile | Asp | Asp | Ser | Trp | Lys | Ser | Ile | Lys | |
| 225 | | | | | 230 | | | | | 235 | | | | | 240 | |
| agt | atc | ttg | gac | tgg | aca | tct | ttt | aac | cag | gag | aga | att | gtt | gat | gtt | 768 |
| Ser | Ile | Leu | Asp | Trp | Thr | Ser | Phe | Asn | Gln | Glu | Arg | Ile | Val | Asp | Val | |
| | | | | 245 | | | | | 250 | | | | | 255 | | |
| gct | gga | cca | ggg | ggt | tgg | aat | gac | cca | gat | atg | tta | gtg | att | ggc | aac | 816 |
| Ala | Gly | Pro | Gly | Gly | Trp | Asn | Asp | Pro | Asp | Met | Leu | Val | Ile | Gly | Asn | |
| | | | 260 | | | | | 265 | | | | | 270 | | | |
| ttt | ggc | ctc | agc | tgg | aat | cag | caa | gta | act | cag | atg | gcc | ctc | tgg | gct | 864 |
| Phe | Gly | Leu | Ser | Trp | Asn | Gln | Gln | Val | Thr | Gln | Met | Ala | Leu | Trp | Ala | |
| | | 275 | | | | | 280 | | | | | 285 | | | | |
| atc | atg | gct | gct | cct | tta | ttc | atg | tct | aat | gac | ctc | cga | cac | atc | agc | 912 |
| Ile | Met | Ala | Ala | Pro | Leu | Phe | Met | Ser | Asn | Asp | Leu | Arg | His | Ile | Ser | |
| | 290 | | | | | 295 | | | | | 300 | | | | | |
| cct | caa | gcc | aaa | gct | ctc | ctt | cag | gat | aag | gac | gta | att | gcc | atc | aat | 960 |
| Pro | Gln | Ala | Lys | Ala | Leu | Leu | Gln | Asp | Lys | Asp | Val | Ile | Ala | Ile | Asn | |
| 305 | | | | | 310 | | | | | 315 | | | | | 320 | |
| cag | gac | ccc | ttg | ggc | aag | caa | ggg | tac | cag | ctt | aga | cag | gga | gac | aac | 1008 |
| Gln | Asp | Pro | Leu | Gly | Lys | Gln | Gly | Tyr | Gln | Leu | Arg | Gln | Gly | Asp | Asn | |
| | | | | 325 | | | | | 330 | | | | | 335 | | |
| ttt | gaa | gtg | tgg | gaa | cga | cct | ctc | tca | ggc | tta | gcc | tgg | gct | gta | gct | 1056 |
| Phe | Glu | Val | Trp | Glu | Arg | Pro | Leu | Ser | Gly | Leu | Ala | Trp | Ala | Val | Ala | |
| | | | 340 | | | | | 345 | | | | | 350 | | | |
| atg | ata | aac | cgg | cag | gag | att | ggt | gga | cct | cgc | tct | tat | acc | atc | gca | 1104 |
| Met | Ile | Asn | Arg | Gln | Glu | Ile | Gly | Gly | Pro | Arg | Ser | Tyr | Thr | Ile | Ala | |
| | | 355 | | | | | 360 | | | | | 365 | | | | |
| gtt | gct | tcc | ctg | ggt | aaa | gga | gtg | gcc | tgt | aat | cct | gcc | tgc | ttc | atc | 1152 |
| Val | Ala | Ser | Leu | Gly | Lys | Gly | Val | Ala | Cys | Asn | Pro | Ala | Cys | Phe | Ile | |
| | 370 | | | | | 375 | | | | | 380 | | | | | |
| aca | cag | ctc | ctc | cct | gtg | aaa | agg | aag | cta | ggg | ttc | tat | gaa | tgg | act | 1200 |
| Thr | Gln | Leu | Leu | Pro | Val | Lys | Arg | Lys | Leu | Gly | Phe | Tyr | Glu | Trp | Thr | |
| 385 | | | | | 390 | | | | | 395 | | | | | 400 | |
| tca | agg | tta | aga | agt | cac | ata | aat | ccc | aca | ggc | act | gtt | ttg | ctt | cag | 1248 |
| Ser | Arg | Leu | Arg | Ser | His | Ile | Asn | Pro | Thr | Gly | Thr | Val | Leu | Leu | Gln | |
| | | | | 405 | | | | | 410 | | | | | 415 | | |
| cta | gaa | aat | aca | atg | cag | atg | tca | tta | aaa | gac | tta | ctt | taa | | | 1290 |
| Leu | Glu | Asn | Thr | Met | Gln | Met | Ser | Leu | Lys | Asp | Leu | Leu | | | | |
| | | | 420 | | | | | 425 | | | | | | | | |

```
<210> SEQ ID NO 14
<211> LENGTH: 429
<212> TYPE: PRT
<213> ORGANISM: Homo sapiens

<400> SEQUENCE: 14
```

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Val Thr Gln Met Ala Leu Trp Ala
    275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

```
Thr Gln Leu Leu Pro Val Lys Arg Lys Leu Gly Phe Tyr Glu Trp Thr
385                 390             395                 400

Ser Arg Leu Arg Ser His Ile Asn Pro Thr Gly Thr Val Leu Leu Gln
            405             410                 415

Leu Glu Asn Thr Met Gln Met Ser Leu Lys Asp Leu Leu
            420             425
```

METHOD FOR PRODUCTION OF RECOMBINANT HUMAN ALPHA-GALACTOSIDASE A FROM MATERIAL CONTAINING CONTAMINANT HOST CELL PROTEINS BY CHROMATOGRAPHY

TECHNICAL FIELD

The present invention generally relates to a method for production of human alpha-galactosidase A (rh alpha-Gal A) using host cells, and to a method for purification of the rh alpha-Gal A produced thereby from a material containing contaminant host cell proteins. More specifically the present invention relates to a process for production of rh alpha-Gal A by culturing rh alpha-Gal A-producing mammalian cells in a serum-free medium, as well as to a process for purification of thus produced rh alpha-Gal A from the culture supernatant using column chromatography including dye-affinity column chromatography, in high yield and to such a high purity as permitting direct use of the purified protein as a medical drug.

BACKGROUND ART

Alpha-galactosidase A (alpha-Gal A) is a lysosomal enzyme having an activity to hydrolyze the terminal alpha-galactosyl bond of glycolipids and glycoproteins. Trihexosylceramide, which contains three hexose moieties, is one of the substrates for alpha-galactosidase A and receives hydrolysis at its terminal hexose moiety by the enzyme. Human alpha-Gal A is expressed as a precursor peptide comprising 429 amino acids, of which N-terminal 31 amino acids constitute a signal peptide. The precursor is processed to the mature peptide, which consists of 398 amino acids left behind after the removal of the signal peptide, and a pair of the mature peptide molecules readily form a homodimer, wherever condition allows, which is the enzymatically active form of human alpha-Gal A. Human alpha-Gal A possesses oligosaccharide chains containing mannose-6-phosphate residues and can be targeted to the lysosome via a mannose-6-phosphate receptor.

Fabry's disease is an X-linked inherited lysosomal storage disease, which is caused by inherited abnormality of gene encoding alpha-Gal A. Lack of the activity of this enzyme causes accumulation of trihexosylceramide in various tissues, resulting in renal impairment, angiokeratomas, and cardiovascular abnormalities, including ventricular enlargement and mitral valve insufficiency.

It had already been known in the 1960's that the enzymatic activity of alpha-galactosidase A is scarcely or only weakly detected in the tissues of patients with Fabry's disease. It thus had been speculated that some inherited abnormality of the gene encoding alpha-Gal A should be the cause of Fabry's disease. Based on this speculation, alpha-Gal A replacement therapy for Fabry's disease had been conducted by infusing alpha-Gal A extracted and purified from human plasma or spleen to the patient, resulting in the confirmation that alpha-Gal A replacement therapy could lower the levels of trihexosylceramide in the blood of the patients suffering from Fabry's disease (see NPL 1, NPL 2, NPL 3). Therefore it had been considered that alpha-Gal A enzyme replacement therapy must be promising for Fabry's disease. Practical application of alpha-Gal A replacement therapy, however, has been extremely limited due to lack of supply of this enzyme.

In 1986, the gene encoding human alpha-Gal A was isolated (see NPL 4), and further, in 1988, a method was reported for expression and production of rh alpha-Gal A by using CHO cells transformed with a human alpha-Gal A expression vector (see NPL 5). Utilizing recombinant technology, these finding made it possible to produce human alpha-Gal A in a large scale, and to use the enzyme as a medicament for the enzyme replacement therapy for Fabry's disease. The rh alpha-Gal A has also been expressed in insect cells (PTL 1).

Further, some methods for purification of rh alpha-Gal A were reported comprising employment of hydrophobic column chromatography, heparin sepharose column chromatography, hydroxylapatite column chromatography, anion-exchange column chromatography, and gel filtration column chromatography (PTL 2, PTL 3). Although the purity of the rh alpha-Gal A obtained by the method for purification described in PTL 2 or PTL 3 has shown to be sufficiently high, it was not considered to be fully acceptable for human use. The reason is that while any medicaments to be infused to patients are required to be free of contaminants, such as, in particular, proteins derived from the host cells employed, either PTL 2 or PTL 3 fails to show whether such contaminants remain in the purified rh alpha-Gal A or not. And further a method for purification of rh alpha-Gal A were reported comprising employment of anion-exchange column chromatography, hydrophobic column chromatography, column chromatography employing as solid phase a material having affinity for phosphate group, cation-exchange column chromatography, and gel filtration column chromatography, in the order (PTL 4). However the PTLs are silent on contamination of rh alpha-Gal A with host cell proteins.

Currently, medical drugs for Fabry's disease containing rh alpha-Gal A as an active ingredient have been on the market under the trade names such as Replagal™ and Fabrazyme™.

CITATION LIST

Patent Literature

[PTL 1]
WO 90/11353
[PTL 2]
WO 98/11206
[PTL 3]
WO 00/53730
[PTL 4]
WO 14/017088

Non Patent Literature

[NPL 1]
Mapes et al: Science 169: 987-9 (1970)
[NPL 2]
Brady et al: N. Engl. J. Med. 289: 9-14 (1973)
[NPL 3]
Desnick et al: Proc Natl Acad Sci USA 76: 5326-30 (1979).
[NPL 4]
Bishop et al: Proc Natl Acad Sci USA 83: 4859-63 (1986)
[NPL 5]
Bishop et al: Lipid Storage Disorders-Biological and Medical Aspects, NY Plenum Press P809-823 (1988)

SUMMARY OF INVENTION

Technical Problem

Against the above background, it is an objective of the present invention to provide a method for production and purification of recombinant human alpha-galactosidase A (rh alpha-Gal A) starting with culturing rh alpha-Gal A producing mammalian cells in a serum-free medium.

It is another objective of the present invention to provide a process for purification of rh alpha-Gal A from a culture supernatant containing contaminant host cell proteins, through column chromatography including dye-affinity column chromatography, in high yield and to such a high purity as permits direct use of the purified protein as a medical drug.

Solution to Problem

The present inventors found that rh alpha-Gal A contained in the supernatant of a culture of rh alpha-Gal A-producing cells in a serum-free medium, can be purified from the supernatant which contains contaminant host cell proteins to a very high purity, and in a very high yield as well, by subjecting the rh alpha-Gal A to a purification process comprising a combination of anion-exchange column chromatography, hydrophobic column chromatography, chromatography using a column having affinity for phosphate group, cation-exchange column chromatography, dye-affinity column chromatography, and gel filtration column chromatography. The present invention was completed through further studies based on the finding.

Thus, the present invention provides what follows:

1. A method for production of a recombinant human alpha-Gal A comprising the steps of:
   (a) culturing recombinant human alpha-Gal A-producing mammalian cells in a serum-free medium to let them secrete the recombinant human alpha-Gal A in the medium,
   (b) collecting culture supernatant by removing the cells from the culture that is obtained in step (a) above,
   (c) subjecting the culture supernatant collected in step (b) above to anion-exchange column chromatography to collect the recombinant human alpha-Gal A-active fractions,
   (d) subjecting the fractions collected in step (c) above to hydrophobic column chromatography to collect recombinant human alpha-Gal A-active fractions,
   (e) subjecting the fractions collected in step (d) above to a column chromatography employing as solid phase a material having affinity for phosphate group to collect the recombinant human alpha-Gal A-active fractions,
   (f) subjecting the fractions collected in step (e) above to cation-exchange column chromatography to collect the recombinant human alpha-Gal A-active fractions,
   (g) subjecting the fractions collected in step (f) above to dye-affinity column chromatography to collect the recombinant human alpha-Gal A-active fractions, and
   (h) subjecting the fractions collected in step (g) above to gel filtration column chromatography to collect the recombinant human alpha-Gal A-active fractions, in the order.

2. The method according to (1) above, wherein the cation exchanger employed in the cation-exchange column chromatography is a weak cation exchanger.

3. The method according to (2) above, wherein the weak cation exchanger has a selectivity based on both hydrophobic interaction and hydrogen bond formation.

4. The method according to (2) or (3) above, wherein the weak cation exchanger has phenyl groups, amide bonds and carboxyl groups.

5. The method according to one of (1) to (4) above, wherein the dye employed in the dye-affinity column chromatography is a blue triazine dye.

6. The method according to one of (1) to (5) above, wherein the material having affinity for phosphate group is selected from the group consisting of hydroxyapatite and fluoroapatite.

7. The method according to (6) above, wherein the material having affinity for phosphate group is hydroxyapatite.

8. The method according to one of (1) to (7) above, wherein the mammalian cells are CHO cells transfected with an expression vector which is designed to express the recombinant human alpha-Gal A under the regulation of EF-1(alpha) promoter.

9. A recombinant human alpha-Gal A composition produced by the method according to one of (1) to (8) above.

10. A medicament comprising the composition according to (9) above administered periodically to a patient.

11. The medicament according to (10) above, wherein the medicament is administered to the patient by injection.

Advantageous Effects of Invention

The present invention enables purification of rh alpha-Gal A from a material containing contaminant host cell proteins. Recombinant human alpha-Gal A thus purified is suitable for use as a medicament in enzyme replacement therapy (ERT) for Fabry's disease. In this therapy, rh alpha-Gal A must be administered periodically to the patient suffering from Fabry's disease. Therefore if an alpha-Gal A medicament contains host cell proteins, ERT using the medicament could have a potential risk to induce a severe antigen-antibody reaction in patients (i.e. anaphylaxis) against host cell proteins. Such a risk can be minimized by using rh alpha-Gal A purified according to the present invention as the medicament. Further, as it has enabled to produce rh alpha-Gal A starting with serum-free culturing of cells, the present invention provides rh alpha-Gal A which is free of any serum-derived contaminants, including pathogenic agents such as viruses or prions. Therefore, the rh alpha-Gal A obtained according to the present invention can be administered into a human body as a safe medicament substantially without any risks of exposure to such pathogenic agents. Further, as it has enabled purification of rh alpha-Gal A substantially avoiding any use of organic solvents, the present invention eliminates the risk of denaturation of rh alpha-Gal A which otherwise might be caused by the exposure to an organic solvent employed. Furthermore, the present invention is favorable to the environment, for the waste fluid left after performing the purification process according to it does not contain an organic solvent, and in the economic sense as well, for it requires no facility to dispose of organic solvents which would otherwise be contained in the waste fluid.

Further the present invention enables highly selective purification of rh alpha-Gal A having mannose-6-phosphate residue in its oligosaccharide chain. To exert its enzymatic activity after administration to a human body, the rh alpha-Gal A must be taken up by relevant cells through mannose-6-phosphate receptors expressed on their surface. Therefore, the highly selective purification achieved according to the present invention will give an rh alpha-Gal A product as a medicament with dramatically increased efficacy.

BRIEF DESCRIPTION OF DRAWINGS

FIG. 1 shows a schematic diagram illustrating the method for construction of vector pE-neo/hGHpA.

FIG. 2-1 shows a first part of a schematic diagram illustrating the method for construction of vector pE-gs/hGHpA(alpha-Gal A).

FIG. 2-2 shows a second part of a schematic diagram illustrating the method for construction of vector pE-gs/hGHpA(alpha-Gal A).

FIG. 3 shows a growth curve of recombinant cells for expression of rh alpha-Gal A and the concentration of rh alpha-Gal A in the culture medium.

FIG. 4 shows the result of SDS-PAGE electrophoresis of the purified rh alpha-Gal A. In lane 1, 5 micrograms of purified rh alpha-Gal A was applied.

FIG. 5 shows a SE-HPLC chart of the purified rh alpha-Gal A. The vertical and horizontal axes show absorbance at 215 nm and retention time, respectively.

DESCRIPTION OF EMBODIMENTS

In the present invention, while the recombinant human alpha-galactosidase A (rh alpha-Gal A) is preferably a recombinant protein of human wild-type alpha-Gal A, it is not excluded that the rh alpha-Gal A is a mutant-type protein having one or more substitution, deletion, addition, and/or insertion of one or more amino acids as compared with the amino acid sequence of human wild-type alpha-Gal A. The DNA sequence for human wild-type alpha-Gal A and amino acid sequence encoded by it, including N-terminal signal sequence, are shown as SEQ ID NO:13 and SEQ ID NO:14, respectively. The N-terminal signal sequence consists of 31 amino acids and is removed post-translationally.

In the present invention, the term "recombinant human alpha-Gal A-producing mammalian cells" or "rh alpha-Gal A-producing mammalian cells" means mammalian cells which have been artificially manipulated to express, or strongly express, the gene encoding human alpha-Gal A. Though in general the gene to be strongly expressed is one which is introduced to the mammalian cells (transformation) using an expression vector in which the gene is incorporated, it may also be an intrinsic gene which has been artificially modified to be strongly expressed. Examples of the means for artificially modifying an intrinsic gene to make it strongly express itself include, but not limited to, replacement of the promoter upstream of the intrinsic gene with a promoter which strongly induces expression of the gene. Such methods have been disclosed in several literatures (i.e. WO94/12650, WO95/31560). Though there is no particular limitation as to which mammalian cells are to be employed, preferred are those of human-, mouse- or Chinese hamster-origin, and, among others, CHO cells, which originate from Chinese hamster ovary cells, are particularly preferred.

In the present invention, the term "recombinant human alpha-galactosidase A" or "rh alpha-Gal A" means the human alpha-galactosidase A which is secreted by the above-mentioned recombinant human alpha-Gal A-producing mammalian cells in the medium during culture.

In the present invention, the term "oligosaccharide chain" means a chain of oligosaccharides covalently bound to the peptide chain of alpha-Gal A, including an asparagine type sugar chain, which is covalently bound to an asparagine residue of alpha-Gal A.

In the present invention, an example of preferable serum-free media in which the rh alpha-Gal A-producing mammalian cells are to be cultured is the following medium which comprises; 3-700 mg/mL of amino acids, 0.001-50 mg/L of vitamins, 0.3-10 g/L of monosaccharides, 0.1-10000 mg/L of inorganic salts, 0.001-0.1 mg/L of trace elements, 0.1-50 mg/L of nucleosides, 0.001-10 mg/L of fatty acids, 0.01-1 mg/L of biotin, 0.1-20 micrograms/L of hydrocortisone, 0.1-20 mg/L of insulin, 0.0-10 mg/L of vitamin $B_{12}$, 0.01-1 mg/L of putrescine, 10-500 mg/L of sodium pyruvate, and water-soluble iron compounds. As desired, it may also include thymidine, hypoxanthine, a conventional pH indicator, and antibiotics.

Further, DMEM/F12 medium, a mixed medium consisting of DMEM and F12, may also be used as a basic serum-free medium. Both of these media are well known to those skilled in the art. As a serum-free medium, DMEM (HG)HAM modified (R5) medium may be used, too, which contains sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium, such as CDoptiCHO™, CHO-S-SFM II or CD CHO (Invitrogen), IS CHO-V™ or IS CHO-V-GS™ (Irvine Scientific), EX-CELL™ 325 PF CHO or EX-CELL™ CD (SIGMA), or the like.

In the present invention, rh alpha-Gal A-producing mammalian cells are cultured for rh alpha-Gal A production in the culture medium for at least 5 days, more preferably for 8 to 14 days. Then the culture supernatant containing rh alpha-Gal A is collected and provided to the purification process for rh alpha-Gal A.

Each of the chromatography procedures for purification of the rh alpha-Gal A from a culture supernatant containing contaminant host cell proteins may, when needed, be carried out in the presence of a nonionic surfactant in order to prevent nonspecific binding of the protein. Though there is no particular limitation as to which nonionic surfactant is to be employed, a polysorbate-based surfactant is preferably employed, and more preferably polysorbate 80 or polysorbate 20. The concentration of such a nonionic surfactant is preferably 0.005% (w/v) to 0.05% (w/v), more preferably about 0.01% (w/v).

The process for purification of the rh alpha-Gal A may be carried out at room temperature or at lower temperatures, but preferably at lower temperatures, particularly at 1-10 deg C.

In the first chromatography step for the purification process, the pH of the culture supernatant is adjusted preferably to 7.0-8.0, more preferably to pH 7.2-7.8, and further preferably to about pH 7.5. Then the culture supernatant is applied to the anion-exchange column that has been equilibrated with a phosphate buffer supplemented with a salt to let rh alpha-Gal A bind to the column. The pH of this phosphate buffer is preferably to 7.0-8.0, more preferably about 7.2-7.8, and still more preferably about 7.5. Though there is no particular limitation as to which salt is to be added to the phosphate buffer, sodium chloride and potassium chloride are preferred. In the case where sodium chloride is used, its concentration is preferably in the range of 5-100 mM, more preferably in the range of 10-60 mM, and still more preferably about 50 mM.

After the anion-exchanger column to which rh alpha-Gal A is bound is washed, the rh alpha-Gal A is eluted using a phosphate buffer with increased salt concentration. Though there is no particular limitation as to which salt is to be used, sodium chloride and potassium chloride are preferred. In the case where sodium chloride is used, its concentration is preferably in the range of 125-500 mM, more preferably 175-350 mM, and still more preferably about 225 mM.

Further, though there is no particular limitation as to which anion-exchanger resin is to be employed, strong anion-exchanger resin may be used preferably. Commercially available resins, such as Q Sepharose Fast Flow (GE Healthcare), may be used preferably.

The hydrophobic column chromatography, the second step of the purification process, is a step for removing contaminants making use of the hydrophobic interaction between rh alpha-Gal A and hydrophobic ligand attached to the resin. Though there is no particular limitation as to which hydrophobic ligand is to be employed in the hydrophobic column chromatography, preferable is a ligand containing phenyl group, and more preferable a ligand containing phenyl group attached to the resin via a spacer arm, such as represented by the formula R—O—CH$_2$—CH(OH)—CH$_2$—O—C$_6$H$_5$ where R denotes the resin. A particularly preferred column material for this is Phenyl Sepharose 6 Fast Flow (GE Healthcare) in which phenyl group is covalently immobilized to Sepharose 6 Fast Flow matrix via a certain spacer arm.

The hydrophobic column chromatography column is equilibrated with a phosphate buffer supplemented with a salt. The pH of this phosphate buffer is preferably 6.5-7.5, more preferably about 6.7-7.3, and still more preferably about 7.0. Though there is no particular limitation as to which salt is to be added to the phosphate buffer, sodium chloride and potassium chloride are preferred. In the case where sodium chloride is used, its concentration is preferably in the range of 500 mM-1 M, and more preferably in the range of 700-800 mM, and still more preferably about 750 mM. Concurrently, Tris buffer may be added to the phosphate buffer at the concentration of preferably 30-70 mM, more preferably about 50 mM.

Then, rh alpha-Gal A-containing fractions of the eluate obtained in the first step are applied to the column. After the column to which rh alpha-Gal A is bound is washed, the rh alpha-Gal A is eluted. Elution may be done by a phosphate buffer not supplemented with salt, where the concentration of phosphate buffer is preferably 3-10 mM, and still more preferably about 5 mM. Concurrently, Tris buffer may be added to the phosphate buffer at the concentration of preferably 30-70 mM, more preferably about 50 mM. Alternatively elution may be done by pure water.

The column chromatography employing a solid phase having affinity for phosphate group, the third step of the purification, is a step to eliminate contaminant proteins, such as carboxyl peptidases. Though there is no particular limitation as to which solid phase is to be used having affinity for phosphate group, hydroxyapatite and fluoroapatite may preferably be used, and hydroxyapatite is particularly preferred.

When a hydroxyapatite column is used, it is equilibrated with a phosphate buffer supplemented with a salt. The pH of this phosphate buffer is preferably 6.5-7.5, more preferably about 6.8-7.2, and still more preferably about 7.0, and the concentration of phosphate preferably 3.0-20 mM, more preferably about 3-15 mM, and further preferably about 10 mM. Though there is no particular limitation as to which salt is to be added to the phosphate buffer, sodium chloride and potassium chloride are preferred. In the case where sodium chloride is used, its concentration is preferably lower than 800 mM, and more preferably in the range of 10-200 mM, and further preferably about 50 mM. Concurrently, Tris buffer may be added to the phosphate buffer at the concentration of preferably 30-70 mM, more preferably about 50 mM.

Then rh alpha-Gal A-containing fractions of the eluate obtained in the second step are applied to the column. After the column to which rh alpha-Gal A is bound is washed, the rh alpha-Gal A is eluted. Elution may be done by a phosphate buffer containing a salt. The pH of this phosphate buffer is preferably 6.5-7.5, more preferably about 6.7-7.3, and still more preferably about 7.0, and the concentration of phosphate is preferably in the range of 30-80 mM, more preferably in the range of 40-60 mM, and still more preferably about 45 mM. Though there is no particular limitation as to which salt is to be used, sodium chloride and potassium chloride are preferred. In the case where sodium chloride is used, its concentration is preferably lower than 300 mM, more preferably in the range of 10-200 mM, and still more preferably of about 50 mM.

The cation-exchange column chromatography, the fourth step of the purification process, is a step to eliminate contaminant proteins. Though there is no particular limitation as to which cation-exchanger is to be employed in the cation-exchange column chromatography, a weak cation exchanger is preferred, and more preferred is a weak cation exchanger having a selectivity based on both hydrophobic interaction and hydrogen bond formation. For example, a weak cation exchanger having phenyl groups, amide bonds and carboxyl groups and having a selectivity based on both hydrophobic interaction and hydrogen bond formation, such as Capto MMC (GE Healthcare), etc., may be employed In the cation-exchange column chromatography, the column is equilibrated with an acetate buffer supplemented with a salt. The pH of this acetate buffer is preferably 4.5-6.5, more preferably about 5.0-6.0, and still more preferably about 5.5. Though there is no particular limitation as to which salt is to be added to the phosphate buffer, sodium chloride, potassium chloride and calcium chloride are preferred. In the case where sodium chloride is used, its concentration is preferably in the range of 50-250 mM, and more preferably in the range of 100-200 mM, and still more preferably about 150 mM.

Then rh alpha-Gal A-containing fractions of the eluate obtained in the third step are applied to the column. After the column to which rh alpha-Gal A is bound is washed, the rh alpha-Gal A is eluted using a phosphate buffer with an increased pH, which is preferably in the range of about 5.5-7.5, more preferably in the range of about 6.0-7.0 and still more preferably about 6.5.

The dye-affinity chromatography, the fifth step of the purification, is a process for removing contaminants, i.e. host cell protein (HCP). Blue triazine dye is preferably used, but other triazine dyes are also suitable. Particularly preferred is Blue Sepharose 6 FF, Fast Flow (GE Healthcare) shown in the following schematic formula, which consists of Sepharose 6 Fast Flow matrix to which a dye, Cibacron™ Blue F3GA, is attached by a covalent bond.

[CHEM 1]

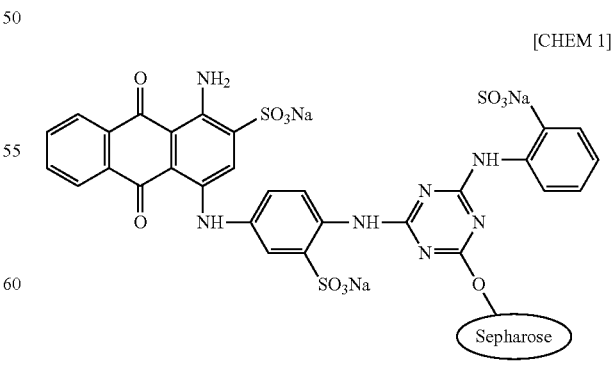

The dye-affinity chromatography column is equilibrated at or near the neutral pH, preferably pH 6.8-7.2, more preferably about pH 7.0 with phosphate buffer supplemented with a salt. Though there is no particular limitation as to which salt is to be added to the phosphate buffer, sodium chloride, and potassium chloride are preferred. In the case where sodium chloride is used, its concentration is preferably in the range of 50-150 mM, and more preferably in the range of 100-150 mM, and still more preferably about 125 mM.

Then, fractions of the eluate obtained in the fourth step are applied to the column. After the column to which rh alpha-Gal A is bound is washed, the rh alpha-Gal A is eluted using phosphate buffer containing an increased concentration of a salt. Though there is no particular limitation as to which salt is to be added to the phosphate buffer, sodium chloride, and potassium chloride are preferred. In the case where sodium chloride is used, its concentration is preferably in the range of 400-750 mM, and more preferably in the range of 400-500 mM, and still more preferably about 450 mM. Trometamol (tris(hydroxymethyl)aminomethane) may concurrently be added to the buffer at the concentration of preferably 40-60 mM, and more preferably at about 50 mM.

The gel filtration column chromatography, the sixth step of the purification process, is a step for elimination of low molecular-weight impurities, such as endotoxins, as well as multimeric complexes or decomposition products of rh alpha-Gal A. Thus, substantially pure rh alpha-Gal A is obtained through the first to sixth steps of the purification process.

Additionally one more column chromatography may be incorporated into the purification process mentioned above, comprising anion-exchange chromatography, dye-affinity column chromatography, hydrophobic column chromatography, column chromatography employing a solid phase having affinity for phosphate group, cation-exchange column chromatography, and gel filtration column chromatography. Such an additional column chromatography is preferably dye-affinity column chromatography, which may be employed between two adjacent steps of the purification process mentioned above as desired.

A step for virus inactivation may optionally be added to the purification process of the present invention. Though there is no particular limitation as to which process for virus inactivation is to be applied, a solvent-detergent method may preferably be applied. For this, a nonionic surfactant is added to a solution containing rh alpha-Gal A, and the resulting mixture is incubated for more than 3 hours. Though there is no particular limitation as to which surfactant is to be used, polysorbate 20, polysorbate 80, triton X-100, and tri(n-butyl)phosphate may preferably be used alone or in any combinations, and more preferably the combination of polysorbate 80 and tri(n-butyl)phosphate may be used.

Such an additional step for virus inactivation may be employed either prior to the purification process or between any two adjacent steps of the purification process mentioned above.

Further, the present invention also provides a method for purification of rh alpha-Gal A from a material containing contaminant host cell proteins. The method includes a step in which a solution containing rh alpha-Gal A and proteins inherent in host cells which were employed to produce rh alpha-Gal A is subjected to dye-affinity column chromatography. The major purpose of this step is to eliminate contaminant host cell proteins. The step can be combined with at least one other purification step selected from cation-exchange column chromatography, hydrophobic column chromatography, anion-exchange column chromatography, column chromatography employing a solid phase having affinity for phosphate group (i.e. hydroxyapatite column chromatography) and gel filtration column chromatography, in any order. Preferably, the combination is anion-exchange column chromatography, hydrophobic column chromatography, column chromatography employing a solid phase having affinity for phosphate group, cation-exchange column chromatography, dye-affinity column chromatography, and gel filtration column chromatography in the order.

A recombinant human alpha-Gal A composition produced by the method according to the present invention is suitable for use in preparation of a medicament to be administered periodically to a patient. The medicament is to be administered to the patient preferably by intravenous injection, more preferably by intravenous infusion, and may be administered to the patient preferably once weekly to once every 2 to 4 weeks, more preferably once every two weeks. The amount of rh alpha-Gal A in one administration to a patient may be preferably 0.1 to 2 mg per kg of body weight, more preferably 0.1 to 2 mg per kg of body weight. The medicament may be supplied in the form of prefilled syringe.

The present invention is described in further detail below with reference to examples. However, it is not intended that the present invention be limited to the examples.

Example 1

Construction of pE-gs/hGHpA(alpha-GalA), a rh alpha-Gal A expression vector pEF/myc/nuc vector (Invitrogen) was digested with KpnI and NcoI to cut out a DNA fragment including the EF-1(alpha) promoter and its first intron, which then was blunt-ended with T4 DNA polymerase. Then the DNA fragment thus prepared was inserted into pC1-neo vector (Invitrogen) which had been digested with BglII and EcoRI and then blunt-ended with T4 DNA polymerase. Inserted into this was the above-mentioned blunt-ended fragment including the EF-1(alpha) promoter and its first intron to give pE-neo7 vector (FIG. 1).

A DNA fragment containing poly adenylation signal sequence of human growth hormone gene was synthesized by annealing four synthetic oligonucleotides: (a) hGH-f1 (ID NO:1), (b) hGH-r1 (SEQ ID NO:2), (c) hGH-f2 (SEQ ID NO:3), and (d) hGH-r2 (SEQ ID NO:4). The DNA fragment thus prepared was inserted between the MluI and KpnI sites of pE-neo7 to give pE-neo/hGHpA vector (FIG. 1).

A 5' half of Chinese hamster Glutamine synthetase ("Ch GS" or "GS") coding region was amplified by PCR using a primer set, GS-1 (SEQ ID NO:5) and GS-3 (SEQ ID NO:6), and, as a template, ssDNA prepared from RNA extracted from CHO cells. A 3' half of Ch GS coding region was amplified by PCR using a primer set, GS-2 (SEQ ID NO:7) and GS-4 (SEQ ID NO:8), and, as a template, ssDNA prepared from RNA extracted from CHO cells. Then the amplified 5' half of Ch GS coding region was ligated into pT7blue-T vector (EMD Millipore). The vector thus obtained was digested with EcoRV and BamHI, and then the amplified 3' half of CH GS coding region, after digestion with EcoRV and BamHI, was inserted into the digested vector to obtain a plasmid vector containing the full length cDNA for Ch-GS. The plasmid obtained was designated pT7blue(GS) (FIG. 2-1).

A 5' half of human alpha-GalA coding region was amplified by PCR using a primer set, GAL-Mlu (SEQ ID NO:9) and GAL-Sca2 (SEQ ID NO:10), and, as a template, human placental Quick-Clone™ cDNA (Clontech). A 3' half of human alpha-GalA coding region was amplified by PCR using a primer set, GAL-Sca1 (SEQ ID NO:11) and GAL-Xba (SEQ ID NO:12), and, as a template, human placental Quick-Clone™ cDNA (Clontech). Then both PCR products were ligated into the EcoRV site of pBluescriptSK(+) vector. The 5' half of human alpha-GalA coding region then was excised from the vector thus obtained, by digestion with MluI and Scat and the 3' half of human alpha-GalA coding region was excised from the vector by digestion with ScaI and NotI Then the excised fragments were concomitantly inserted into the MluI and NotI sites of the multi cloning site in pE-neo vector to obtain full length cDNA for human alpha-GalA. The plasmid thus obtained was designated pE-neo(alpha-GalA) (FIG. 2-2).

pE-neo/hGHpA was digested with AflII and BstXI, and into the vector thus digested was inserted Ch-GS cDNA which had been excised out from pT7blue(GS) by digestion with AflII and BstXI. The plasmid obtained was designated pE-gs/hGHpA (FIG. 2-1). pE-gs/hGHpA vector was digested with MluI and NotI, and into the vector thus digested was inserted human alpha-GalA cDNA which had been excised out from pE-neo(alpha-GalA) by digestion with MluI and NotI. The plasmid obtained, designated pE-gs/hGHpA(alpha-GalA), was used as rh alpha-Gal A expression vector in further experiments (FIG. 2-2).

Example 2

Production of Recombinant Cells for Expression of rh alpha-Gal A

CHO cells (CHO-K1: purchased from American Type Culture Collection) was transfected with the above-mentioned expression vector pE-gs/hGHpA(alpha-Gal A) using Lipofectamine™ 2000 (Invitrogen) according to the following method. Briefly, two days before transfection, $2.5 \times 10^5$ CHO-K1 cells were seeded in a 3.5-cm culture dish containing 3 mL of D-MEM/F12 medium containing 5% FCS (D-MEM/F12/5% FCS), and the cells were cultured at 37 deg C. in a humidified atmosphere of 5% $CO_2$ and 95% air. After two days of culture, the cells were washed with PBS, and 1 mL of fresh serum-free D-MEM/F12 medium was added. Then the cells were transfected by addition of 200 microliters of a 1:1 mixture solution consisting of Lipofectamine™ 2000 solution diluted 20 times with Opti-MEM™ I medium (Life Technologies) and a pE-gs/hGHpA (alpha-GalA) solution diluted to 20 micrograms/mL with Opti-MEM™ I medium, followed by incubation at 37 deg C. in a humidified atmosphere of 5% $CO_2$ and 95% air for 5 hours. After transfection, the medium was replaced with D-MEM/F12/5% FCS and cultivation followed for 24 hours.

Then, the medium was replaced with glutamine-free GMEM-S medium (SIGMA) supplemented with 1× GS supplement (SIGMA), 10% dialyzed FBS and 30 micromole/L methionine sulfoximine (MSX), and a selective culture was carried out at 37 deg C. in a humidified atmosphere of 5% $CO_2$ and 95% air. Cells that had grown in the medium for selective culture were subjected to several successive rounds of subculture in the medium to give recombinant cells. In the course of the selective culture, concentration of MSX in the medium was elevated step by step to amplify the inserted recombinant genes. Finally bulk cells that stably grew in the medium with 300 micromole/L MSX were obtained after two steps subculture at elevated MSX concentrations (100 and 300 micromole/L MSX).

Then, according to the limiting dilution technique, the cells having the amplified recombinant gene were seeded on a 96-well plate in such a manner that not more than one cell might be seeded per well. The cells then were cultured for about 10 days to let each of them form a monoclonal colony. The culture supernatant in the wells where a monoclonal colony was formed was each sampled and examined for human alpha-Gal A activity as described below, and cell lines which were found expressing a high activity for human alpha-Gal A were selected.

For adaptation to serum-free suspension cell culture, the selected cell lines were each cultured in a commercially available serum-free medium, CD-OptiCHO™ medium (Invitrogen) supplemented with 10 mg/L insulin, 40 mg/L thymidine, 100 mg/L hypoxantine and 100 micromole/L MSX, at 37 deg C. in a humidified atmosphere of 5% $CO_2$ and 95% air until the cells stably grew. The cells then were suspended in CD-OptiCHO™ medium (Invitrogen) supplemented with 10 mg/L insulin, 40 mg/L thymidine, 100 mg/L hypoxantine, 100 micromole/L MSX, and 10% DMSO, and stored as seed cells in liquid nitrogen.

Example 3

Culture of Recombinant Cells for Expression of rh alpha-Gal A

The above seed cells were thawed and diluted to a density of $4 \times 10^5$ cells/mL and cultured for 3 to 4 days with CD-OptiCHO™ medium supplemented with 10 mg/L insulin, 40 mg/L thymidine, 100 mg/L hypoxantine and 100 micromole/L MSX (CD medium), and then diluted to a density of $2 \times 10^5$ cells/mL with CD medium and cultured for 3 to 4 days. These cells were again diluted to a density of $2 \times 10^5$ cells/mL with CD medium and further cultured for 3 to 4 days.

The number of the cells thus cultured was counted, and the cell culture was diluted with CD medium to a density of $2 \times 10^5$ cells/mL, and then the cells in 1 L of the diluted culture were cultured with shaking for a few days. The scale of culture was escalated until the culture volume reached 200 L.

Then the number of the cells was counted, and the cells were diluted to a density of $2 \times 10^5$ cells/mL with 1800 L of CD-OptiCHO™ medium supplemented with 10 mg/L insulin, 40 mg/L thymidine, 100 mg/L hypoxantine and 0.1% HY soy (Invitrogen), and cultured for 11 days. 22.4 L of feed solution which contained 8.84 g insulin, 35.2 mmol hypoxantine, 5.6 mmol thymidine and 1.8 kg HY soy in CD-OptiCHO™ medium was added on the 3rd, 5th, 7th, and 9th days. Sampling was made every day during the culture, and measurement was performed for cell number, survival rate, glucose concentration, and amount of expressed rh alpha-Gal A. In the case where glucose concentration became lower than 3 g/L, 30% glucose solution was added so that the concentration reached 3.5 g/L. During the 11 days of culture, the viable cell density and the concentration of rh alpha-Gal A were daily monitored. The viable cell density reached about $6 \times 10^6$ cells/mL on days 6-7 of culture, indicating that high-density cell culture was successfully achieved (FIG. 3). As measured by ELISA as described below, the concentration in the medium of rh alpha-Gal A secreted by the cells increased over time and reached almost 140 mg/L on day 6 (FIG. 3).

After completion of the culture above, the cell culture was collected and filtered successively through Millistak+™ HC Pod Filter grade D0HC, (Millipore), Millistak+™ HC Pod Filter grade X0HC (Millipore), and then Durapore Opticap™ XLT20 (0.22 micrometer, Millipore), to give a culture supernatant. The obtained culture supernatant was concentrated by a hollow fiber module equipped with PS membrane (polysulfone membrane) to one 13th of the original volume.

Example 4

Virus Inactivation

Tri-n-butyl phosphate (TNBP) and polysorbate 80 were added to the approximately 75 L of the concentrated culture supernatant described above so that their final concentrations would be 0.3% (v/v) and 1% (w/v), respectively, and this mixture solution then was gently stirred for 3 to 4 hours at room temperature.

Example 5

Method for Purification of rh alpha-Gal A

The pH of the above virus-inactivated solution then was adjusted to 7.5 by addition of 1 M Tris-buffer (pH 8.8), and subsequently the conductivity was adjusted to that of the 10 mM phosphate buffer (pH7.5) containing 50 mM NaCl, by addition of 50 mM phosphate buffer (pH 7.0) containing 1 M NaCl. Then the solution was filtered through Durapore Opticap™ XL10 (Millipore), and then was loaded on a Q Sepharose Fast Flow column (column volume: about 19.2 L, bed height: about 20 cm, GE Healthcare), an anion-exchange column, which had been equilibrated with 10 mM phosphate buffer (pH 7.5) containing 50 mM NaCl at a linear flow rate of 150 cm/hr to allow rh alpha-Gal A to be adsorbed by the column. Then, the column was washed with a threefold column volume of the same buffer supplied at the same flow rate, and the adsorbed rh alpha-Gal A then was eluted with a sixfold column volume of 10 mM phosphate buffer (pH 7.5) containing 225 mM NaCl, subsequently with a threefold column volume of 50 mM phosphate buffer (pH 7.0) containing 1 M NaCl, and the fractions containing rh alpha-Gal A were collected.

To the fractions collected at the step of Q Sepharose Fast Flow column chromatography above, one fourth volume of 2 M NaCl was added to adjust the concentration of NaCl to about 500 mM, and subsequently acetic acid was added to adjust the pH to 7.0. The solution obtained was loaded on a Phenyl Sepharose 6 Fast Flow column (column volume: 19.2 L, bed height: about 20 cm, GE Healthcare), a hydrophobic column, which had been equilibrated with 50 mM Tris-HCl, 5 mM phosphate buffer (pH 7.0) containing 750 mM NaCl, at a linear flow rate of 150 cm/hr to allow rh alpha-Gal A to be adsorbed by the column. Then after the column was washed with a threefold column volume of the same buffer supplied at the same flow rate, the adsorbed rh alpha-Gal A was eluted with a ninefold column volume of a buffer consisting of 50 mM Tris-HCl and 5 mM phosphate (pH 7.0), and subsequently with a threefold column volume of pure water, and the fractions containing rh alpha-Gal A were collected.

The fractions collected at the step of Phenyl Sepharose 6 Fast Flow column chromatography above, was loaded on a CHT-I ceramic hydroxyapatite column (column volume: 19.2 L, bed height: about 20 cm, Bio-Rad Laboratories), a hydroxyapatite column, which had been equilibrated with 50 mM Tris-HCl, 10 mM phosphate buffer (pH 7.0) containing 50 mM NaCl, at a linear flow rate of 150 cm/hr to allow rh alpha-Gal A to be adsorbed by the column. Then, the column was washed with a fivefold column volume of the same buffer supplied at the same flow rate, and the adsorbed rh alpha-Gal A then was eluted with a ninefold column volume of a buffer containing 50 mM Tris-HCl, 45 mM sodium phosphate and 50 mM NaCl (pH 7.0), and subsequently with a threefold column volume of 200 mM phosphate buffer (pH7.0) and the fractions containing rh alpha-Gal A were collected.

To the fractions collected at the step of CHT-I ceramic hydroxyapatite column chromatography above, acetic acid was added to adjust the pH to 5.5. A precipitate formed by this was removed by filtration through Opticap™ SHC XL5 (0.22 micrometer, Millipore). The solution obtained was loaded on a Capto™ MMC column (column volume: 6.3 L, bed height: about 20 cm, GE Healthcare), a cation-exchange column having a selectivity based both on hydrophobic interaction and on hydrogen bond formation, which had been equilibrated with 50 mM acetate buffer (pH 5.5) containing 150 mM NaCl, at a linear flow rate of 300 cm/hr to allow rh alpha-Gal A to be adsorbed by the column. Then after the column was washed with a fourfold column volume of the same buffer supplied at the same flow rate, the adsorbed rh alpha-Gal A was eluted with a fivefold column volume of 50 mM phosphate buffer (pH6.5), and subsequently with a threefold column volume of 50 mM phosphate buffer (pH7.0) containing 1 M NaCl, and the fractions containing rh alpha-Gal A were collected.

To the fractions collected at the step of Capto™ MMC column chromatography above, 1M Tris buffer (pH8.8) was added to adjust the pH to 7.0. Half of the solution obtained was loaded on Blue Sepharose 6FF column (column volume: about 19.2 L, bed height: about 20 cm, GE Healthcare) equilibrated with 20 mM phosphate buffer (pH 7.0) containing 125 mM NaCl, supplied at a linear flow rate of 150 cm/hr to allow rh alpha-Gal A to be adsorbed by the column. And then, the column was washed with a threefold column volume of 20 mM phosphate buffer (pH 7.0) containing 125 mM NaCl supplied at the same flow rate, and the adsorbed rh alpha-Gal A then was eluted with a fourfold column volume of 50 mM Tris-HCl/5 mM phosphate buffer (pH 7.0) containing 450 mM NaCl supplied at the same flow rate, and the fractions containing rh alpha-Gal A were collected. The other half of the solution was sequentially processed by dye-affinity column chromatography in the same manner as described above. The collected fractions containing rh alpha-Gal A were combined for further purification.

The fractions collected at the step of dye-affinity column chromatography above was concentrated using Pellicon™ 3 Cassettes equipped with Biomax™ 30 membrane (Millipore) until the total volume became less than 1 L. One third of the concentrated solution was loaded on a Superdex™ 200 prep grade column (column volume: about 58 L, bed height: about 30 cm×2, GE Healthcare) which had been equilibrated with 20 mM phosphate buffer (pH 5.8) containing 137 mM NaCl. The same buffer then was supplied at a linear flow rate of 25 cm/hr, and the fractions which corresponded to the main peak observed by absorbance at 280 nm were collected as fractions containing purified rh alpha-Gal A. This chromatography was carried out three times to purify all the concentrated solution above, and the fractions collected by each run were combined.

The fractions pooled at the step of Superdex™ 200 prep grade column chromatography above were concentrated by Hollow fiber module equipped with PS membrane, and to the concentrated solution, polysorbate 80 was added at the final concentration of 0.02%. The obtained solution was filtered through Viresolve™ Pro Modus1.3 (0.07 m² size, Millipore) to avoid any possible contamination with viruses and microorganisms in the final product.

In each step of purification, the amount of rh alpha-Gal A contained in the loaded material and that of recovered rh alpha-Gal A in the collected fractions were quantified using ELISA as described below. The results are shown in Table 1. In the table, "rh alpha-Gal A recovery rate/step" means the proportion of the amount of recovered rh alpha-Gal A in the step to that of rh alpha-Gal A loaded in the step, and "rh alpha-Gal A recovery rate/total" the proportion of the amount of recovered rh alpha-Gal A in the step to the initial amount of rh alpha-Gal A subjected to the purification process. The initial amount of rh alpha-Gal A subjected to the purification process was 140.6 g, of which 91.4 g was finally recovered, thus giving the rh alpha-Gal A recovery rate/total as high as 65.0%. These results show that the method for purification described above enables purification of rh alpha-Gal A in very high yield and in a large production scale.

TABLE 1

Recovery rate of rh alfa-Gal A in each purification step

| Purification process | rh α-Gal A loaded (g) | rh α-Gal A recovered (g) | rh α-Gal A recovery rate/ step (%) | rh α-Gal A recovery rate/ total (%) | HCP/ rh α-Gal A (ppm) |
|---|---|---|---|---|---|
| Anion-exchange column (Q Sepharose FF) | 140.6 | 133.5 | 95.0 | 95.0 | $1.9 \times 10^6$ |
| Hydrophobic column (Phenyl Sepharose FF) | 134.4 | 116.9 | 87.0 | 83.1 | $7.0 \times 10^5$ |
| Hydroxyapatite column (CHT-I) | 116.4 | 110.5 | 94.9 | 78.6 | $8.5 \times 10^4$ |
| Cation-exchange column (Capto MMC) | 109.8 | 105.4 | 96.0 | 75.0 | $8.6 \times 10^3$ |
| Dye-affinity column (Blue 6FF) | 106.2 | 102.9 | 96.9 | 73.2 | $2.5 \times 10^2$ |
| Gel filtration column (Superdex 200 pg) | 101.2 | 91.4 | 90.3 | 65.0 | 20 |

Example 6

Analysis of Human alpha-Gal A by ELISA

To each well of a 96-well microtiter plate (Nunc) was added 100 microliters of mouse anti-human alpha-Gal A monoclonal antibody diluted to 0.25 micrograms/mL with 0.05 M carbonate-bicarbonate buffer (pH 9.6), and the plate was left untouched for at least 1 hour at room temperature or overnight at 2-8 deg C. to allow the antibody to be absorbed by the wells. Then, after each well was washed with phosphate buffered saline, pH 7.4 (PBS) containing 0.05% Tween 20 (PBS-T), 300 microliters of PBS-T containing 1% BSA was added, and the plate was left untouched for at least one hour at room temperature. Then, after each well was washed three times with PBS-T, 100 microliters of the test sample or human alpha-Gal A standard, which had been diluted as desired with PBS containing 0.5% BSA and 0.05% Tween 20 (PBS-BT), was added to the well, and the plate was left untouched for at least one hour at room temperature. Then, after each well was washed three times with PBS-T, 100 microliters of horseradish peroxidase-labeled rabbit anti-human alpha-Gal A polyclonal antibody diluted with PBS-BT was added and the plate was left untouched for at least one hour. Then, after each well was washed three times with PBS-T, 100 microliters of 0.4 mg/mL o-phenylenediamine with phosphate-citrate buffer (pH 5.0) containing 0.009% hydrogen peroxide was added to the well, and the plate was left untouched for 10 to 25 minutes at room temperature. Then 0.1 mL of 1 mol/L $H_2SO_4$ was added to each well to stop the reaction, and the optical density at 490 nm was measured for the well on a 96-well plate reader.

Example 7

Measurement of the Activity of rh alpha-Gal A

Standard solutions were prepared by dissolving 4-methyumbelliferone in Dilution Buffer (26.7 mM Citrate-44.8 mM phosphate buffer, pH 4.6 containing 0.1 mg/mL BSA) at concentrations of 0 to 200 micromole/L. A substrate solution was prepared by dissolving 4-methylumbelliferyl-alpha-D-galactopyranoside (SIGMA) in Dilution Buffer at the final concentration of 5 mM. 10 microliters of each of the standard solutions or the test sample diluted with Dilution Buffer was added to each well of a 96-well microtiter plate (FluoroNunc Plate, Nunc). 75 microliters of the substrate solution was added to each well containing the diluted test sample or any of the standard solutions, and the plate was left untouched for one hour at 37 deg C. in the dark. After this incubation, 200 microliters of Stop Buffer (0.2 M glycine-NaOH, pH 10.6) was added to each well. Then fluorescent intensity of the solution in each well was measured by a 96-well plate reader with excitation light at the wavelength of 335 nm and fluorescent light at the wavelength of 460 nm.

A standard curve was produced by plotting fluorescence intensity measured of the standard solutions and interpolating between the plotted data points. The fluorescence intensity of each sample was corresponded to the concentration of the released 4-MUF using the standard curve. The specific activity of human alpha-Gal A was calculated as Units/mg, where one Unit of activity was equal to one micromole of 4-MUF produced per minute at 37 deg C. A published US patent application (publication No. 2004-0229250) was referred to for conducting the above measurement of the activity of rh alpha-Gal A. The specific activity of rh alpha-Gal A purified by the process described above was found to be about 50 U/mg (48.3 to 53.7 U/mg).

Example 8

Analysis of Purity of rh alpha-Gal A

Five micrograms of the rh alpha-Gal A purified above was subjected to SDS-PAGE electrophoresis under a reductive, heating (70 deg C. 10 min.) condition. The gel-stained with Coomassie brilliant blue revealed a single band corresponding to rh alpha-Gal A in Superdex™ 200 pg fraction (FIG. 4).

Further, rh alpha-Gal A purified above was analyzed by Size-elimination HPLC (SE-HPLC). HPLC was performed using LC-20A System, SPD-20AV UV/VIS Detector (Shimazu Corp.). For SE-HPLC analysis, 10 microliters of a sample solution containing 2 mg/mL of rh alpha-Gal A purified above was applied onto TSKgel G3000SW$_{XL}$ column (7.8 mm I.D.×30 cm, TOSOH) equilibrated with 25 mM phosphate buffered saline (PBS) at a flow rate of 0.5 ml/min. Elution profile was produced by monitoring absorbance at 215 nm.

The SE-HPLC analysis of the above purified rh alpha-Gal A revealed a single peak alone (FIG. 5). The results showed that the rh alpha-Gal A obtained above was highly purified and free of any detectable contaminants. This result demonstrates that the rh alpha-Gal A purified above is of such a high purity as may be directly used as a medical drug.

Example 9

Measurement of Host Cell Proteins (HCPs)

The amount of contaminant host cell proteins (HCPs) present in the pool of collected rh alpha-Gal A-active fractions in each of the purification steps 1 to 6 was quantified by ELISA in a conventional manner and compared with the amount of rh alpha-Gal A contained in the pool. The results are presented in Table 1 as "HCP/rh alpha-Gal A (ppm)", which is the ratio in mass of HCPs to rh alpha-Gal A. As shown in Table 1, the ratio, after the final step of purification, was as low as 20 ppm, a level which is low enough to allow the rh alpha-Gal A thus purified to be used as a medicament administered to a human repeatedly by injection.

Among the steps of the purification process, the fifth, the dye-affinity chromatography, was most effective to remove HCPs from the rh alpha-Gal A contaminated with it. Namely, in this step, almost 97% of HCPs were removed and the rate of HCPs/rh alpha-Gal A decreased from $8.6 \times 10^3$ ppm to $2.5 \times 10^2$ ppm. The result shows that dye-affinity chromatography is a remarkably effective way to remove HCPs from rh alpha-Gal A preparation.

INDUSTRIAL APPLICABILITY

The present invention is utilized for production of rh alpha-galactosidase A (rh alpha-Gal A) in a large scale, with a sufficiently high purity to be administered as a medicament to a patient suffering from Fabry's syndrome.

SEQUENCE LISTING FREE TEXT

SEQ ID NO:1=hGH-f1, synthetic sequence
SEQ ID NO:2=hGH-r1, synthetic sequence
SEQ ID NO:3=hGH-f2, synthetic sequence
SEQ ID NO:4=hGH-r2, synthetic sequence
SEQ ID NO:5=Primer GS-1, synthetic sequence
SEQ ID NO:6=Primer GS-3, synthetic sequence
SEQ ID NO:7=Primer GS-2, synthetic sequence
SEQ ID NO:8=Primer GS-4, synthetic sequence
SEQ ID NO:9=Primer GAL-Mlu, synthetic sequence
SEQ ID NO:10=Primer GAL-Sca2, synthetic sequence
SEQ ID NO:11=Primer GAL-Sca1, synthetic sequence
SEQ ID NO:12=Primer GAL-Xba, synthetic sequence

SEQUENCE LISTING

GP183-PCT ST25.txt

---

The invention claimed is:

1. A method for production of a recombinant human alpha-Gal A comprising the steps of:
    (a) culturing recombinant human alpha-Gal A-producing mammalian cells in a serum-free medium to let them secrete the recombinant human alpha-Gal A in the medium,
    (b) collecting culture supernatant by removing the cells from the culture that is obtained in step (a) above,
    (c) subjecting the culture supernatant collected in step (b) above to anion-exchange column chromatography to collect the recombinant human alpha-Gal A-active fractions,
    (d) subjecting the fractions collected in step (c) above to hydrophobic column chromatography to collect recombinant human alpha-Gal A-active fractions,
    (e) subjecting the fractions collected in step (d) above to a column chromatography employing as solid phase a material having affinity for phosphate group to collect the recombinant human alpha-Gal A-active fractions,
    (f) subjecting the fractions collected in step (e) above to cation-exchange column chromatography to collect the recombinant human alpha-Gal A-active fractions,
    (g) subjecting the fractions collected in step (f) above to dye-affinity column chromatography to collect the recombinant human alpha-Gal A-active fractions, by using a dye affinity column equilibrated at pH 6.8-7.2 with phosphate buffer supplemented with 100-150 mM sodium chloride and eluting the recombinant human alpha-Gal A using a phosphate buffer containing 400-750 mM sodium chloride and 40-60 mM tris(hydroxymethyl) aminomethane, and
    (h) subjecting the fractions collected in step (g) above to gel filtration column chromatography to collect the recombinant human alpha-Gal A-active fractions, in the order.

2. The method according to claim 1, wherein the cation exchanger employed in the cation-exchange column chromatography is a weak cation exchanger.

3. The method according to claim 2, wherein the weak cation exchanger has a selectivity based on both hydrophobic interaction and hydrogen bond formation.

4. The method according to claim 2, wherein the weak cation exchanger has phenyl groups, amide bonds and carboxyl groups.

5. The method according to claim 1, wherein the dye employed in the dye-affinity column chromatography is a blue triazine dye.

6. The method according to claim 1, wherein the material having affinity for phosphate group is selected from the group consisting of hydroxyapatite and fluoroapatite.

7. The method according to claim 6, wherein the material having affinity for phosphate group is hydroxyapatite.

8. The method according to claim 1, wherein the mammalian cells are CHO cells transfected with an expression vector which is designed to express the recombinant human alpha-Gal A under the regulation of EF-1(alpha) promoter.

* * * * *